Aug. 23, 1949. E. B. HAGLER Plant Pat. 866
CAMELLIA JAPONICA PLANT
Filed Sept. 9, 1947
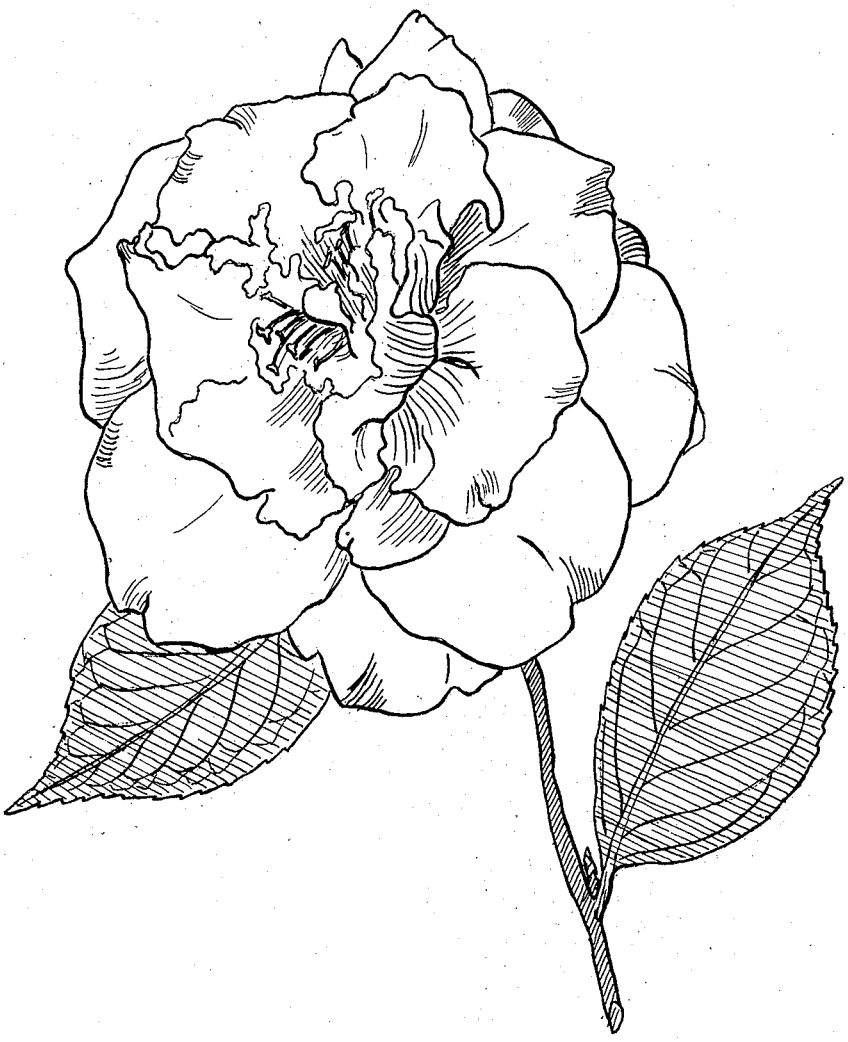
Cecilia B. Barnett
Witness
Elizabeth Bussell Hagler
Applicant Patented Aug. 23, 1949

Plant Pat. 866

UNITED STATES PATENT OFFICE

866

CAMELLIA JAPONICA PLANT

Elizabeth Burdell Hagler, Augusta, Ga., assignor to J. Laurence Sprunt, trading as Orton Nursery, Wilmington, N. C.

Application September 9, 1947, Serial No. 773,066

1 Claim. (Cl. 47—60)

This is a distinct and new variety of *Camellia japonica* plant, which I have asexually reproduced. The parentage of the plant is unknown. It derives from a seedling and not a sport. The seed was planted in the fall of 1937 and the first bloom appeared in October 1943.

The single figure of the drawing shows a fully open flower, with a stem and two leaves.

A detailed description of the plant follows:

Classification:
- *Botanic.*—*Camellia japonica.*

Blooming habit:
- *Blooms.*—Early; October 1 to November 15.

Bud:
- *Size.*—Large.
- *Form.*—Oval.

Bloom:
- *Size.*—Large; 4″ to 5″ when fully expanded.
- *Borne.*—Singly.
- *Stems.*—Strong.
- *Form.*—Incomplete double. Central part composed of numerous white petaloids, with stamens intermixed.
- *Petalage.*—Petals in 2 rows. Number—14 plus. Size—1½–1¾″ wide by 2–2½″ long.
- *Color.*—Pure white.

Petals:
- *Texture.*—Medium thickness, soft.
- *Appearance.*—Like satin.
- *Form.*—Ovate outline with retuse tip.
- *Arrangement.*—Imbricated.
- *Fragrance.*—Faint.
- *Lastingness.*—On the plant, very long; as cut flower, long.

Genital organs:
- *Stamens.*—Filaments—white; anthers—yellow; singly and in fascicles of 2 to 3 intermixed with numerous petaloids.
- *Pistil.*—Stigma—white; style—white; ovary—tricarpellary; usually 3 ovules.

Fruit: Has not borne.

Form: Shrub.

Growth: Medium, upright, branching, compact.

Foliage:
- *Size.*—Medium, 2½″ wide x 4″ long.
- *Quantity.*—Abundant.
- *Color.*—New foliage—Moss Green, glossy, changing to Boxwood Green, glossy, as leaves age. Old foliage—Boxwood Green, not so glossy.
- *Shape.*—Ovate; apex—acuminate; base—rounded.
- *Texture.*—Leathery, glossy, smooth; underside smooth.
- *Ribs and veins.*—Not prominent; pinnate; net-veined.
- *Edge.*—Serrate.

Wood:
- *New wood.*—Moss Green, glossy, when tender to mahogany when hard. Bark, smooth.
- *Old wood.*—Brown. Bark, smooth.

My claim for Letters Patent is based on the fact that the present variety is a pure white *Camellia japonica* with a very early blooming season. It has the advantage of blooming before frost, between October 1 and November 15 and is the only self-white with this characteristic. Its early blooming season coincides with that of the colored varieties Daikagura Variegated, Daikagura Red, and Arajishi (red, sometimes showing specks of white).

I claim:

The new and distinct variety of *Camellia japonica* plant as described and illustrated, characterized by the self-white flower blooming before frost.

ELIZABETH BURDELL HAGLER.

No references cited.